(12) United States Patent
Thomas et al.

(10) Patent No.: US 10,603,103 B2
(45) Date of Patent: Mar. 31, 2020

(54) END EFFECTOR FOR ELECTROSURGICAL INSTRUMENT

(71) Applicant: GYRUS MEDICAL LIMITED, Cardiff (GB)

(72) Inventors: Daniel John Thomas, Cardiff (GB); Lewis Meurig Jones, Cardiff (GB); Andrew Edward Jenkins, Rhondda Cynon Taff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 371 days.

(21) Appl. No.: 14/993,496

(22) Filed: Jan. 12, 2016

(65) Prior Publication Data
US 2016/0199124 A1 Jul. 14, 2016

(30) Foreign Application Priority Data

Jan. 14, 2015 (GB) .................................. 1500532.5
Feb. 13, 2015 (GB) .................................. 1502479.7

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00083* (2013.01); *A61B 2018/00178* (2013.01)

(58) Field of Classification Search
CPC ...... A61B 18/1445; A61B 2018/00083; A61B 2018/00178; A61B 2018/0063
See application file for complete search history.

(56) References Cited

U.S. PATENT DOCUMENTS 6,942,676 B2 * 9/2005 Buelna ................. A61B 17/122
606/151
7,150,097 B2 12/2006 Sremcich et al.
(Continued)

FOREIGN PATENT DOCUMENTS

AU 2006222705 10/2006
EP 1486177 12/2004
(Continued)

OTHER PUBLICATIONS

Letter from UKIPO advising of error in search report dated May 26, 2016 in United Kingdom Patent Application No. GB1522803.4 dated Aug. 23, 2016 and attached Corrected Search Report under Section 17.
(Continued)

*Primary Examiner* — Daniel W Fowler
*Assistant Examiner* — Tigist S Demie
(74) *Attorney, Agent, or Firm* — Oliff PLC

(57) ABSTRACT

An end effector for an electrosurgical instrument includes a pair of opposing first and second jaw members movable between an open position in which the jaw members are disposed in a spaced relation relative to one another, and a closed position in which the jaw members cooperate to grasp tissue therebetween. A first sealing electrode is located on the first jaw member, and a second sealing electrode is located on the second jaw member. One or more stop members are disposed on the sealing electrodes, the one or more stop members being formed of a compliant material such that they are capable of deforming when the jaw members are moved to their closed position with tissue grasped therebetween.

26 Claims, 3 Drawing Sheets

(56) References Cited

U.S. PATENT DOCUMENTS

| | | | |
|---|---|---|---|
| 7,473,253 B2 | 1/2009 | Dycus et al. | |
| 7,877,852 B2 | 2/2011 | Unger et al. | |
| 7,922,953 B2 | 4/2011 | Guerra | |
| 8,241,284 B2 | 8/2012 | Dycus et al. | |
| 9,713,491 B2 | 7/2017 | Roy et al. | |
| 2003/0014053 A1 | 1/2003 | Nguyen et al. | |
| 2003/0181932 A1 | 9/2003 | Buelna | |
| 2004/0122423 A1* | 6/2004 | Dycus | A61B 18/1445 606/51 |
| 2005/0021027 A1* | 1/2005 | Shields | A61B 18/1445 606/51 |
| 2007/0265616 A1 | 11/2007 | Couture et al. | |
| 2008/0015575 A1 | 1/2008 | Odom et al. | |
| 2009/0254081 A1 | 10/2009 | Allison et al. | |
| 2011/0060335 A1 | 3/2011 | Harper et al. | |
| 2012/0083783 A1 | 4/2012 | Davison et al. | |
| 2012/0265241 A1 | 10/2012 | Hart et al. | |
| 2013/0085496 A1 | 4/2013 | Unger et al. | |
| 2013/0226177 A1 | 8/2013 | Brandt et al. | |
| 2013/0255063 A1 | 10/2013 | Hart et al. | |
| 2014/0025073 A1 | 1/2014 | Twomey et al. | |
| 2014/0194875 A1 | 7/2014 | Reschke et al. | |
| 2015/0018816 A1 | 1/2015 | Latimer | |

FOREIGN PATENT DOCUMENTS

| | | |
|---|---|---|
| EP | 1795140 | 6/2007 |
| EP | 2425791 | 3/2012 |
| EP | 2687176 | 1/2014 |
| JP | 2004-532676 A | 10/2004 |
| WO | 2015/197395 A1 | 12/2015 |

OTHER PUBLICATIONS

Examination Report under section 18(3) for corresponding United Kingdom Application No. GB1522803.4 dated Sep. 5, 2016.

Search Report under Section 17(6) for claims 19 and 20 in United Kingdom Patent Application No. GB1522803.4 dated Aug. 23, 2016.

Combined Search and Examination Report Under Sections 17 & 18(3) in UK Application No. GB 1522803.4, dated May 26, 2016.

U.S. Appl. No. 14/992,137, filed Jan. 11, 2016, Jones, et al.

U.S. Appl. No. 14/992,193, filed Jan. 11, 2016, Thomas, et al.

U.S. Appl. No. 14/993,408, filed Jan. 12, 2016, Thomas, et al.

U.S. Appl. No. 14/994,464, filed Jan. 13, 2016, Jones.

Search Report in UK Application No. GB 1500532.5, dated Jun. 5, 2015.

Search Report in UK Application No. GB 1502479.7, dated Jul. 10, 2015.

Oct. 29, 2018 Office Action issued in Chinese Patent Application No. 201610017914.8.

Jul. 2, 2019 Office Action issued in Chinese Patent Application No. 201610017914.8.

Oct. 1, 2019 Office Action issued in Japanese Patent Application No. 2016-004658.

* cited by examiner

END EFFECTOR FOR ELECTROSURGICAL INSTRUMENT

This application claims priority to United Kingdom Application No. 1500532.5 filed 14 Jan. 2015 and United Kingdom Application No. 1502479.7, filed 13 Feb. 2015, the entire contents of each of which are hereby incorporated by reference.

TECHNICAL FIELD

Embodiments of the present invention relate to an end effector for an electrosurgical instrument, and to an electrosurgical instrument for sealing tissue. Such systems are commonly used for the treatment of tissue in surgical intervention, most commonly in "keyhole" or minimally invasive surgery, but also in "open" surgery.

BACKGROUND TO THE INVENTION AND PRIOR ART

It is known to provide an electrosurgical instrument in which the sealing of tissue is effected by means of a pair of jaw elements. U.S. Pat. Nos. 7,473,253 & 8,241,284 are two examples of this kind of instrument. These two patents describe the provision of one or more non-conductive stop members, in order to regulate the spacing between the jaws when tissue is held therebetween.

SUMMARY OF THE INVENTION

Embodiments of the present invention attempt to provide an improvement to an instrument such as those described above.

Accordingly, from one aspect an end effector for an electrosurgical instrument is provided, the end effector comprising a pair of opposing first and second jaw members, at least one of the jaw members being movable relative to the other from a first open position in which the jaw members are disposed in a spaced relation relative to one another, to a second closed position in which the jaw members cooperate to grasp tissue therebetween,
  a first sealing electrode located on the first jaw member,
  a second sealing electrode located on the second jaw member,
  one or more stop members disposed on one or both of the first and second sealing electrodes, the one or more stop members being formed of a compliant material with a Shore A hardness of between 20 and 80, such that they are capable of deforming when the jaw members are moved to their closed position with tissue grasped therebetween.

The provision of one or more compliant stop members provides for a spacing to be maintained between the jaws when tissue is grasped therebetween, but for the compliant stop members to accommodate varying thicknesses of tissue capable of being grasped between the jaws. The compliant stop members are intentionally compressed by the grasping of the tissue, such that the spacing between the jaw members depends on the thickness and condition of the tissue being treated.

Preferably, the one or more stop members are formed of an electrically non-conductive material. This prevents shorting from occurring between the one or more stop members and the sealing electrode opposite the one or more stop members when the jaw members are closed without tissue therebetween.

The one or more compliant stop members are formed of a material with a Shore A hardness of between 20 and 80, typically between 30 and 50, and most preferably between 35 and 45. Convenient materials include fluoroelastomeric materials such as "Perlast"™ or "FKM™". Alternatively, the compliant material is a silicone material. This level of Shore A hardness provides a very compliant material, more than just a slight flexing of a relatively rigid material. Typically, the compliant stop members are capable of deforming by more than 10% when the jaw members are moved to their closed position with tissue grasped therebetween. That is, the height of which the compliant stop members project above the surface of the first and second sealing electrodes may be reduced by more than 10% when the jaws carrying the stop members are closed about tissue, as the stop members compress under the reaction force of the tissue.

Preferably, the end effector includes a plurality of compliant stop members. Typically, the plurality of compliant stop members are such that when the jaw members are moved to their closed position at least one stop member at a first longitudinal position along the jaw members contacts the sealing electrode on the opposite jaw member before at least one stop member at a second longitudinal position along the jaw members contacts the sealing electrode on the opposite jaw member. In this way, the jaws close around tissue in a gradual sequential fashion, closing on the tissue from one end of the jaws. Typically, the first longitudinal position is more distal than the second longitudinal position, with the jaw closure starting at the distal end and progressing proximally.

Conceivably, the one or more compliant stop members deform from a first cross-sectional profile to a second cross-sectional profile when the jaw members are moved to their closed position with tissue grasped therebetween. Typically, the first cross-sectional profile is substantially trapezoidal, and the second cross-sectional profile is that of a truncated triangle with a generally flatter top. In this way, the stop members are compressed into a flatter shape when the jaws are closed around tissue.

Preferably, the one or more compliant stop members comprise one or more elongate members. Conveniently, the one or more elongate members extend longitudinally along one or both of the jaw members, typically extending along the majority of the length of the first and/or second sealing electrodes. Continuous elongate stop members ensure that the tissue is supported wherever it is being grasped along the jaw members, and the compliant nature of the stop members ensures that the jaw spacing is appropriate to the thickness of tissue being contained within the jaws.

Conveniently, there is at least one elongate stop member on each of the first and second sealing electrodes, typically a plurality of elongate stop members on each of the first and second sealing electrodes. One preferred construction has two stop members on each of the first and second jaw members, the stop members being offset one from another. Conceivably, one or both of the first and second sealing electrodes present a generally concave shape when viewed from the side. The longitudinally curved sealing electrode or electrodes, together with the compliant stop members means that the tissue is grasped sequentially by the jaw members as they close one against the other.

Embodiments of the invention further reside in an electrosurgical instrument including
  a handle including an actuating mechanism movable between a first position and a second position, a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween, a first sealing electrode located on the first jaw member, a second sealing electrode located on the second jaw member, electrical connections capable of connecting the instrument to an electrosurgical generator, such that when the jaw members are in their closed position with tissue grasped therebetween, the instrument is capable of sealing the tissue by passing an electrosurgical current into the tissue from the first and second sealing electrodes, and one or more stop members disposed on one or both of the first and second sealing electrodes, the one or more stop members being formed of a compliant material with a Shore A hardness of between 20 and 80, such that they are capable of deforming when the jaw members are moved to their closed position with tissue grasped therebetween.

Further embodiments reside in an end effector for a surgical instrument including a pair of opposing first and second jaw members, at least one of the jaw members being movable relative to the other from a first open position in which the jaw members are disposed in a spaced relation relative to one another, to a second closed position in which the jaw members cooperate to grasp tissue therebetween, a first sealing electrode located on the first jaw member, a second sealing electrode located on the second jaw member, one or more stop members disposed on one or both of the first and second sealing electrodes, the one or more stop members being formed of a compliant material such that they are capable of deforming by at least 10% when the jaw members are moved to their closed position with tissue grasped therebetween.

That is, in one preferred embodiment the compliant material is such that a distance which the stop members project above the surface of the first and/or second sealing electrodes is reduced by more than 10%, and optionally by more than 20%, when the jaws carrying the stop members are moved to their closed position with tissue grasped therebetween.

DESCRIPTION OF THE DRAWINGS

Embodiments of the invention will now be further described, by way of example only, with reference to the accompanying drawings, in which.

DESCRIPTION OF THE EMBODIMENTS

Figure 1:
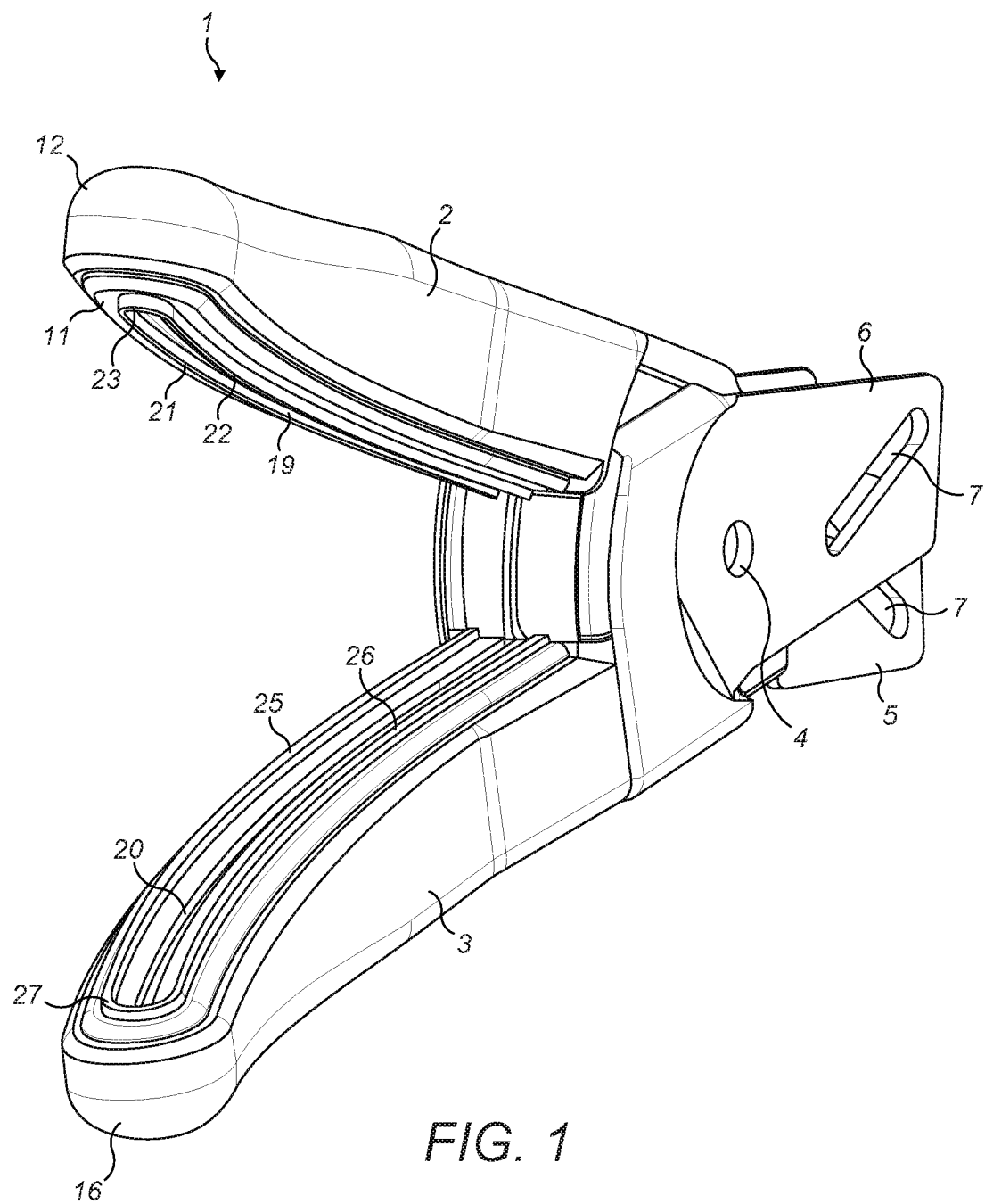
FIG. 1 is a schematic perspective view of an end effector in accordance with an embodiment of the present invention.
Figure 2:
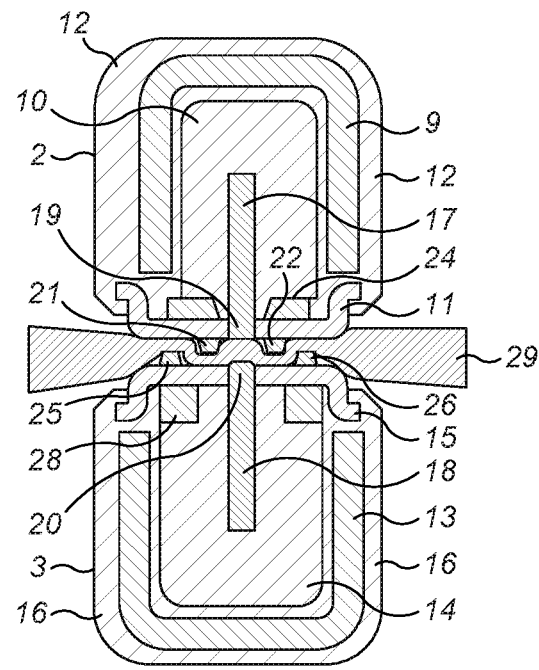
FIG. 2 is an enlarged sectional view of the end effector of FIG. 1.

Referring to FIGS. 1 & 2, an end effector shown generally at 1 comprises an upper jaw 2 pivotably connected to a lower jaw 3 about a pivot 4. Flanges 5 are present at the proximal end of upper jaw 2, while flanges 6 are present at the proximal end of lower jaw 3. The flanges 5 & 6 each have slots 7 through which a drive pin (not shown) extends, such that proximal and distal movement of the drive pin and by means of a drive mechanism (also not shown) which causes the jaws 2 & 3 to pivot between open and closed positions.

The upper jaw 2 comprises a metallic jaw frame 9, inside which is located a plastics insert 10. A metallic shim 11 is present on the inward face of upper jaw 2, with the shim, insert and jaw frame being encased in an overmoulded body 12. Similarly, the lower jaw 3 comprises a metallic jaw frame 13, plastics insert 14 and metallic shim 15, encased in an overmoulded body 16. Inserts 10 & 14 have longitudinal grooves 17 & 18, corresponding also with grooves 19 & 20 in the shims 11 & 15 so as to form an elongate slot for a knife member (not shown).

Elongate stop members 21 & 22 are present on the shim 11, the stop members running parallel to one another along the length of the upper jaw before meeting in a common nose portion 23. The stop members are formed of a compliant material such as silicone or a fluoro-elastomer. The stop members are relatively soft in nature, and have a Shore A hardness of between 20 and 80. Such a soft and compliant nature means that they are capable of deforming by more than 10% when pressure is placed thereon, for example by the jaws being closed with tissue therebetween. That is, the stop members are sufficiently compliant to deform by at least 10% in the direction in which the pressure is applied. For example, the height of the stop members is capable of being reduced by more than 10% when the jaws are closed about tissue. In some embodiments, depending on the softness of the stop members, they may reduce in height by more than 10%, for example by more than 20%, or more than 30%.

The stop members 21 & 22 are moulded onto the shim 11 and secured in place by means of a lower portion 24 received below the shim 11 and joined to the stop members 21 & 22 through holes (not shown) in the shim 11. Similarly, stop members 25 & 26 are present on the shim 15, the stop members running parallel to one another along the length of the lower jaw before meeting in a common nose portion 27. The stop members 25 & 26 are moulded onto the shim 15 and secured in place by means of a lower portion 28 received below the shim 15 in similar fashion to that described with respect to the upper jaw 2. The stop members 25 & 26 are offset with respect to the stop members 21 & 22, with the stop members on the shim 11 running inside those on the shim 15.

When the upper and lower jaws 2 & 3 are pivoted into their closed position, the shims 11 & 15 move adjacent one another, grasping tissue 29 therebetween. The stop members are deformed by the tissue 29 pressing against them, and change shape slightly, as will be further described later. The amount by which the stop members deform will depend on the thickness of the tissue being grasped between the jaws 2 & 3, and also by the hardness of the tissue. The ability of the stop members to deform allows them to compensate for different thicknesses and hardness of tissue, while still maintaining an appropriate separation between the shims 11 & 15.

The shims 11 & 15 are supplied with an electrosurgical coagulating current for an electrosurgical generator (not shown) which causes the tissue 29 to become sealed. The stop members ensure that the shims 11 & 15 do not come into direct contact, and thereby avoid shorting between the shims They also maintain an appropriate separation between the shims 11 & 15 while the tissue is being sealed, this separation being necessary for the effective sealing of tissue.

Figure 3:
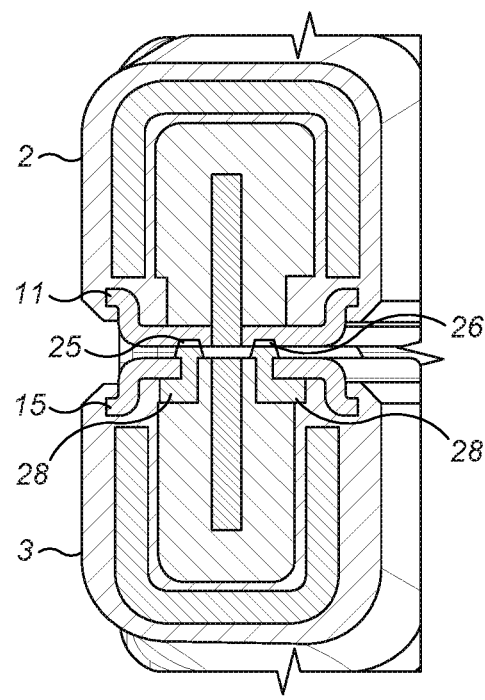
FIG. 3 is an enlarged sectional view of an alternative embodiment of end effector in accordance with the invention.

FIG. 3 shows an alternative construction in which stop members 25 & 26 are only present on the shim 15 and not on the shim 11. The stop members are moulded onto the shim 15 as previously described, using a lower portion 28 and holes (not shown) in the shim 15. Although only two stop members 25 & 26 are provided, they separate the shims 11 & 15 as before, and deform to accommodate different tissue grasped between the jaws 2 & 3.

Figure 4:
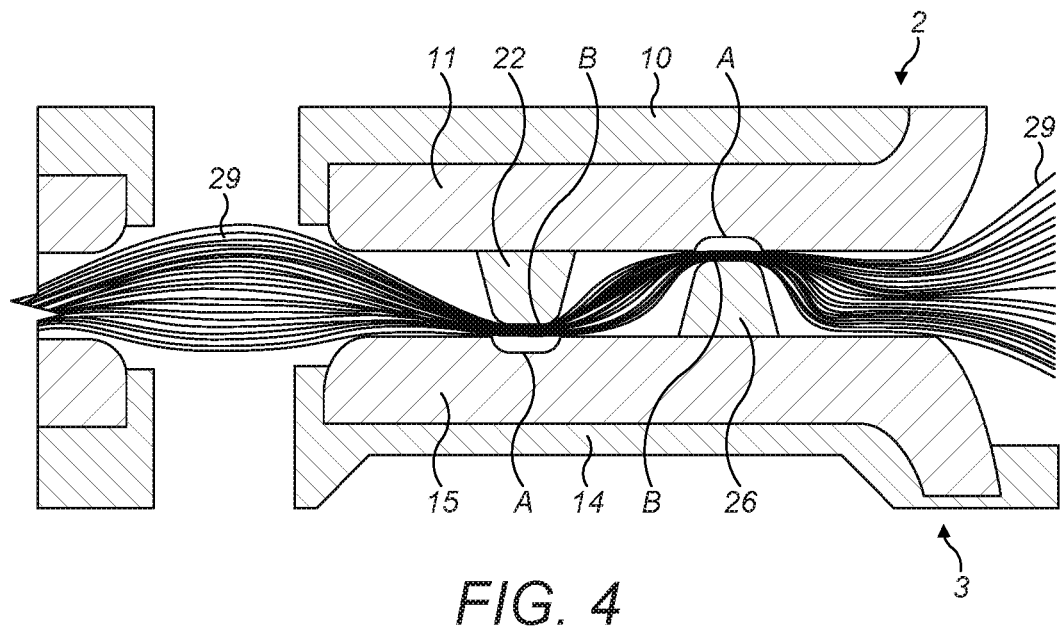
FIG. 4 is a schematic sectional view of the end effector of FIGS. 1 & 2 showing deformation of the stop members.

FIG. 4 shows how the stop members deform when tissue is grasped between the jaws 2 & 3. FIG. 4 shows the shims 11 & 15 and elongate stop members 22 & 26, with tissue 29 grasped between the jaws 2 & 3. As described previously, the stop members are generally compliant, having a Shore A hardness of between 20 and 80. This allows the cross-sectional shape of the stop members to change as pressure is applied thereto when the jaws close. As shown in FIG. 4, the cross-sectional shape of the stop members 22 & 26 was previously generally triangular, as shown at "A", although the point of the triangle is rounded in order to prevent the stop members from damaging tissue, particularly by cutting into it. The grasping of the tissue deforms the stop members 22 & 26 into an even more rounded cross-sectional shape as shown at "B". The deformation of the stop members will vary, both from tissue to tissue, and also at different longitudinal positions along the stop members, depending on the thickness and hardness of the tissue being grasped. Whatever the deformation, the stop members 22 & 26 will maintain an appropriate spacing between the shims 11 & 15, the spacing once again depending on the thickness and hardness of the tissue being grasped.

Figure 5:
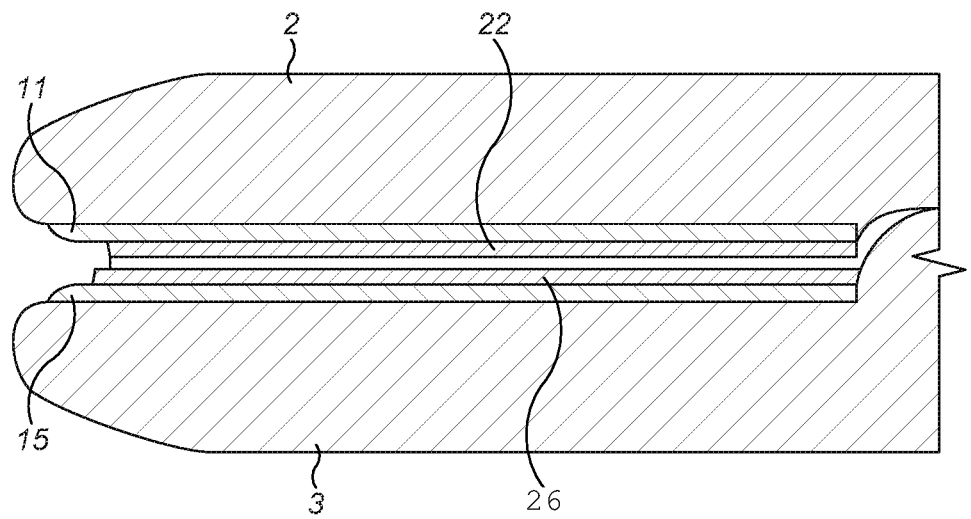
FIG. 5 is a schematic side view of the end effector of FIGS. 1 & 2.

FIG. 5 shows how the separation between the shims 11 & 15 varies along the length of the jaws 2 & 3. As the jaws 2 & 3 are moved into their closed position, the shims 11 & 15 and hence the stop members 22 & 26 are relatively close together towards the distal end of the jaws. However, more proximally, the shims 11 & 15 and hence the stop members 22 & 26 are relatively further apart. This means that as the jaws close, they first grasp tissue towards their distal end, with the grasping of tissue progressing gradually towards the proximal end of the jaws. The jaws 2 & 3 are reasonably flexible, such that they can themselves deform slightly as increased force is applied to the tissue. Not shown in FIG. 5, but the longitudinal profile of the jaws can be non-linear, such that closing of the jaws causes them to change from one curved shape to another, or from a curved shape to a more linear configuration. Whichever configuration of jaws and stop members is employed, the compliant nature of the stop members ensures that the spacing between the shims can vary depending on the thickness and hardness of the tissue being held therebetween.

The elongate compliant stop members also allow for longitudinal compression of the stop members along the length thereof, helping to produce a more uniform jaw spacing regardless of where the tissue is grasped along the length of the jaws. By making the stop members compliant rather than rigid, the jaw spacing is able to change depending on the nature and thickness of the tissue grasped between the jaws, and where and how it is grasped.

The invention claimed is:

1. An end effector for a surgical instrument comprising:
   a pair of opposing first and second jaw members, at least one of the jaw members being movable relative to the other from a first open position in which the jaw members are disposed in a spaced relation relative to one another, to a second closed position in which the jaw members cooperate to grasp tissue therebetween,
   a first sealing electrode located on the first jaw member,
   a second sealing electrode located on the second jaw member, and
   one or more stop members is molded to at least one of the first and second sealing electrodes, wherein:
      the one or more stop members is formed of a compliant material with a Shore A hardness of between 20 and 80, such that the one or more stop members are capable of deforming when the jaw members are moved to the closed position with tissue grasped therebetween,
      the one or more stop members include a lower portion that is located below the at least one of the first and second sealing electrodes,
      the one or more stop members extend through one or more holes in the at least one of the first and second sealing electrodes, and
      the one or more stop members extend along at least a majority of a length of the first and second sealing electrodes.

2. The end effector according to claim 1, wherein the one or more stop members are formed of a material with a Shore A hardness of between 30 and 50.

3. The end effector according to claim 2, wherein the one or more stop members are formed of a material with a Shore A hardness of between 35 and 45.

4. The end effector according to claim 1, wherein the one or more stop members are formed of a material such that the one or more stop members are capable of deforming by more than 10% when the jaw members are moved to their closed position with tissue grasped therebetween.

5. The end effector according to claim 1, wherein the one or more stop members are formed of an electrically non-conductive material.

6. The end effector according to claim 1, further including a plurality of stop members.

7. The end effector according to claim 6, wherein the plurality of stop members are such that when the jaw members are moved to the closed position at least one stop member at a first longitudinal position along the jaw members contacts the sealing electrode on the opposite jaw member before at least one stop member at a second longitudinal position along the jaw members contacts the sealing electrode on the opposite jaw member.

8. The end effector according to claim 7, wherein the first longitudinal position is more distal than the second longitudinal position.

9. The end effector according to claim 1, wherein the one or more compliant stop members deform from a first cross-sectional profile to a second cross-sectional profile when the jaw members are moved to their closed position with tissue grasped therebetween.

10. The end effector according to claim 9, wherein the first cross-sectional profile is trapezoidal.

11. The end effector according to claim 9, wherein the second cross-sectional profile is that of a truncated triangle with a flat top.

12. The end effector according to claim 1, wherein the one or more stop members comprise one or more elongate members.

13. The end effector according to claim 12, wherein the one or more elongate members extend longitudinally along one or both of the jaw members.

14. The end effector according to claim 13, wherein the one or more elongate members extend along a majority of the length of the first and/or second sealing electrodes.

15. The end effector according to claim 12, wherein there is at least one elongate stop member on each of the first and second sealing electrodes.

16. The end effector according to claim 12, wherein there is a plurality of elongate stop members on each of the first and second sealing electrodes.

17. The end effector according to claim 1, wherein one or both of the first and second sealing electrodes present a generally concave shape when viewed from the side.

18. An electrosurgical instrument comprising:
a handle including an actuating mechanism movable between a first position and a second position,
a pair of opposing first and second jaw members, movement of the actuating mechanism from its first position to its second position causing at least one of the jaw members to move relative to the other from a first open position in which the jaw members are disposed in a spaced relation relative to one another, to a second closed position in which the jaw members cooperate to grasp tissue therebetween,
a first sealing electrode located on the first jaw member,
a second sealing electrode located on the second jaw member,
electrical connections capable of connecting the instrument to an electrosurgical generator, such that when the first and second jaw members are in the closed position with tissue grasped therebetween, the instrument is capable of sealing the tissue by passing an electrosurgical current into the tissue from the first and second sealing electrodes, and
one or more stop members secured to at least one of the first and second sealing electrodes, the one or more stop members being formed of a compliant material with a Shore A hardness of between 20 and 80, such that the one or more stop members are capable of deforming when the jaw members are moved to the closed position with tissue grasped therebetween, the one or more stop members including a lower portion that is located below the at least one of the first and second sealing electrodes, the one or more stop members extending through one or more holes in the at least one of the first and second sealing electrodes.

19. An end effector for a surgical instrument comprising:
a pair of opposing first and second jaw members, at least one of the jaw members being movable relative to the other from a first open position in which the jaw members are disposed in a spaced relation relative to one another, to a second closed position in which the jaw members cooperate to grasp tissue therebetween,
a first sealing electrode located on the first jaw member,
a second sealing electrode located on the second jaw member,
one or more stop members secured to at least one of the first and second sealing electrodes, the one or more stop members being formed of a compliant material such that the one or more stop members are capable of deforming by at least 10% when the jaw members are moved to the closed position with tissue grasped therebetween, the one or more stop members including a lower portion that is located below the at least one of the first and second sealing electrodes, the one or more stop members extending through one or more holes in the at least one of the first and second sealing electrodes.

20. The end effector according to claim 19, wherein the compliant material is such that a distance which the stop members project above the surface of the at least one of the first and second sealing electrodes is reduced by more than 10%, and optionally by more than 20%, when the jaw members carrying the stop members are moved to the closed position with tissue grasped therebetween.

21. An end effector for a surgical instrument comprising:
a pair of opposing first and second jaw members, at least one of the jaw members being movable relative to the other from a first open position in which the jaw members are disposed in a spaced relation relative to one another, to a second closed position in which the jaw members cooperate to grasp tissue therebetween,
a first sealing electrode located on the first jaw member,
a second sealing electrode located on the second jaw member,
one or more stop members fixed to at least one of the first and second sealing electrodes, the one or more stop members being formed of a compliant material with a Shore A hardness of between 20 and 80, such that the one or more stop members are capable of deforming when the jaw members are moved to the closed position with tissue grasped therebetween, the one or more stop members being a continuous longitudinal rail extending along at least a majority of a length of the first and second sealing electrodes.

22. The end effector according to claim 21, wherein the one or more stop members are disposed on both of the first and second sealing electrodes.

23. The end effector according to claim 22, wherein the one or more stop members disposed on the first sealing electrode are laterally offset from the one or more stop members disposed on the second sealing electrode.

24. The end effector according to claim 23, wherein there are two longitudinal rails disposed on the first sealing electrode and two longitudinal rails disposed on the second sealing electrode.

25. The end effector according to claim 24, wherein the two longitudinal rails disposed on the first sealing electrode are located inside the two longitudinal rails disposed on the second sealing electrode such that the two longitudinal rails disposed on the first sealing electrode are nearer to the center line of the jaw members.

26. An end effector for a surgical instrument comprising:
a pair of opposing first and second jaw members, at least one of the jaw members being movable relative to the other from a first open position in which the jaw members are disposed in a spaced relation relative to one another, to a second closed position in which the jaw members cooperate to grasp tissue therebetween,
a first sealing electrode located on the first jaw member and having a first tissue sealing surface,
a second sealing electrode located on the second jaw member and having a second tissue sealing surface, and
one or more stop members secured to at least one of the first and second sealing electrodes and projecting above first and/or second tissue sealing surfaces of the first and second sealing electrodes, wherein:
the one or more stop members is formed of a compliant material with a Shore A hardness that is both between 20 and 80 and less than a Shore A hardness of the first and second sealing electrodes, such that the one or more stop members are capable of deforming when the jaw members are moved to the closed position with tissue grasped therebetween, and the one or more stop members extend along at least a majority of a length of the first and second sealing electrodes.

\* \* \* \* \*